United States Patent [19]
Wells

[11] Patent Number: 4,618,344
[45] Date of Patent: Oct. 21, 1986

[54] DEPILATORY COMPOSITIONS

[75] Inventor: Robert L. Wells, Cincinnati, Ohio

[73] Assignee: The Procter & Gamble Company, Cincinnati, Ohio

[21] Appl. No.: 383,433

[22] Filed: Jun. 1, 1982

[51] Int. Cl.$^4$ .......................... A61K 7/155; C14C 1/06
[52] U.S. Cl. ........................................... 8/161; 8/160; 8/94.16
[58] Field of Search .......................... 8/160, 161, 94.16

[56] References Cited

U.S. PATENT DOCUMENTS

| | | | |
|---|---|---|---|
| 2,192,380 | 3/1940 | Jayne | 8/94.16 |
| 2,453,333 | 11/1948 | Moore et al. | 564/233 |
| 3,194,736 | 7/1965 | Brown et al. | 8/161 |
| 3,271,258 | 9/1966 | Rouet | 8/94.16 |
| 3,628,910 | 12/1971 | Grayson | 8/161 |
| 3,686,296 | 8/1972 | Yablonsky | 424/267 |
| 3,728,356 | 8/1973 | Yablonsky | 8/161 |
| 3,981,681 | 9/1976 | de la Guardia | 8/161 |
| 4,121,904 | 10/1978 | Schamper | 8/161 |
| 4,177,260 | 12/1977 | Wajaroff | 8/160 |

FOREIGN PATENT DOCUMENTS 765987 5/1970 Belgium.
2168202 1/1972 France.

OTHER PUBLICATIONS

Moore et al; *J. American Leather Chemists Association*, 28:245–259 (1933).

*Primary Examiner*—Albert T. Meyers
*Assistant Examiner*—F. Abramson
*Attorney, Agent, or Firm*—Douglas C. Mohl; David L. Suter; Richard C. Witte

[57] ABSTRACT

Aqueous depilatory compositions containing aminoguanidine and active thiol agent(s) which provide for faster hair removal are disclosed.

13 Claims, No Drawings

DEPILATORY COMPOSITIONS

TECHNICAL FIELD

The invention described herein relates to a depilatory composition comprised of an accelerator, aminoguanidine, and an active thiol agent.

BACKGROUND OF THE INVENTION

The use of thiol-based depilatory agents, such as thioglycolic acid, for removal of unwanted body and facial hair is well established in the art. These agents react by reducing hair's protein disulfide bonds to sulfhydryl anions, thereby allowing easy removal of the weakened hairs when washed or wiped away. However, in using thiols, it was discovered that certain conditions facilitated the effectiveness of this reaction. One such condition is high alkalinity to provide ionized reactants. Not only do the high pH's (approximately 12.0–12.5) result in ionized thiols, but they also result in increased penetration of a reactant. Substances to provide further enhancement of penetration by active thiols were developed.

Further progress in the area of depilation resulted in the development of compounds which seem to expose more of the disulfide bonds to thiol agents. It is thought that these compounds decrease inter and intra chain bonding in hair keratin thereby, "accelerating" the rate of penetration and thus reaction by the thiols. Ureas, thioureas, and guanidines are thought to react as such accelerators, and in fact, the prior art discloses many of these nitrogen-based depilatory accelerators. Among such prior art references are U.S. Pat. No. 2,192,380, Mar. 5, 1940 to David Walker Jayne, Jr.; U.S. Pat. No. 3,194,736, July 13, 1965 to Ernest Brown & John E. Logan; Belgian Pat. No. 765,987, May 5, 1970 to Investigations Scientifiques Pharmaceutiques; U.S. Pat. No. 3,981,681, Sept. 21, 1976 to Mario de la Guardia; U.S. Pat. No. 3,271,258, Sept. 6, 1966 to Charles Zviak and Jean Rouet; U.S. Pat. No. 4,177,260, Dec. 4, 1977 to Theodor Wajaroff; French Pat. No. 2,168,202, Jan. 20, 1972 to Fabres SA P.; U.S. Pat. No. 3,686,296, Aug. 22, 1972 to Harvey A. Yablonsky; and U.S. Pat. No. 3,728,356, Aug. 17, 1973 to Harvey A. Yablonsky.

Aminoguanidine has been combined with alkaline hydrolyzing agents, such as calcium hydroxide, for unhairing hides and skins, Moore, E.K. and Kopperhoefer, R., *J. American Leather Chemists Association*, 28: 245–259 (1933). However, no thiol depilatory combined with aminoguanidine is suggested by Moore and Kopperhoefer.

The present invention provides not only more effective and faster removal of unwanted body and facial hair than urea accelerators, but the combination of aminoguanidine with a thiol depilatory is safer for human usage in comparison to guanidine and thiourea accelerators.

It is an object of the present invention to provide safe and effective removal of unwanted body and facial hair. It is a further object to provide depilatory compositions containing aminoguanidine and an active thiol depilatory agent. These and other objectives will become readily apparent from the detailed description which follows.

All percentages and ratios used herein are by weight unless otherwise specified.

SUMMARY OF THE INVENTION

This invention relates to depilatory compositions which use aminoguanidine as an accelerator for active thiol depilatory agents.

DESCRIPTION OF THE INVENTION

The depilatory composition of the present invention not only is safer than guanidine and thiourea compounds, but it also reduces depilation time. This reduction in time for removal of unwanted hair is advantageous for several reasons. First of all, the average person using such compositions prefers reduced time of depilatory action. Secondly, this reduction permits less exposure of skin to possible irritation due to high alkalinity or exposure to thiol actives.

The increased rate of hair removal obtained by the present invention is believed to be due to the acceleration by aminoguanidine, allowing the thiol active to more readily exert its depilatory effect.

Essential Components

The composition of the present invention is based upon three essential ingredients, aminoguanidine, a thiol depilatory, and water.

Aminoguanidine, formula presented in the figure below, can be used in base or salt form at concentrations providing from about 0.01M to about 2.0M aminoguanidine, preferably from about 0.5M to about 1.0M aminoguanidine. Suitable salts of aminoguanidine include the hydrochloride form, sulfate form, bicarbonate form, and mixtures thereof.

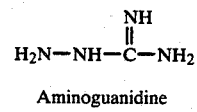

Aminoguanidine

The thiol active may include one or more thiol acids, (e.g. thioglycolic, thiolactic acid, and β-mercaptopropionic acid), or the alkali and/or the alkaline-earth metal salts of these acids. In addition, other active thiol agents can be used. These include α-mercaptoethanol, thioglycerols, 1,3-dithio-2-propanol, 1,4-dithio-2-butanol, 1,4-dimercapto-2,3-butanediol, 1,3-dithio-2-methoxypropane, 1,3-dimercapto-2-aminopropane, 1,4-dimercapto-2,3-diaminobutane, aminoethanethiol, and related effective thiol actives. The thiol active is present at a concentration of from about 0.1M to about 2.0M, preferably from about 0.2M to about 1.0M thiol.

Mixtures of thiol actives also may be used in the compositions described herein.

Water from about 10% to about 80%, preferably from about 20% to about 70%, makes up the third essential component of the present invention.

The pH of the present depilatory composition should range from about 10.5 to about 12.5, preferably from about 11.0 to about 12.3 at 25° C. These pH's preferably are achieved through the use of an alkaline material such as calcium hydroxide.

Optional Components

The present invention can be embodied in several commercial forms such as creams, lotions, gels, aerosols, or the like. If the present invention is put into such forms, a number of optional ingredients would be added. These ingredients include from about 0% to about 5% of a suitable filler such as chalk, magnesium oxide and carbonate, clays, talc, fumed silica and mixtures thereof. Emulsifiers such as anionic surfactants (e.g., fatty alcohol sulfates and/or alkyl aryl sulfates), nonionic surfactants, and mixtures thereof, present at levels of from about 0% to about 20%, are also useful. Often chelating agents to complex with metals are included in such compositions. One suitable example of such a chelator is ethylenediaminetetraacetic acid, its salts and mixtures thereof.

Among the other ingredients useful in these various embodiments is a gelling agent or thickener, present at levels of from about 0% to about 30%. The thickeners used could include both natural and synthetic ones such as tragacanth, xanthan, karaya, and guar gums, clays, methyl or hydroxyethyl cellulose, hydroxypropyl cellulose, carboxymethyl cellulose, fatty and polyvinyl alcohols, modified starches and sugars, and mixtures thereof. Emollients such as paraffin, petrolatum, mineral oil, fatty alcohols, silicone oils, and mixtures thereof present at levels of from about 0% to about 60%, can also be included. Fragrance and coloring generally provide the remaining ingredients.

When the present invention is in the form of an emulsion, it can be either in an oil-in-water or water-in-oil form.

The following are examples of compositions of the invention described herein. They are merely illustrative of the present invention and are not limitative thereof:

EXAMPLE I

| Depilatory Cream | |
|---|---|
| Aminoguanidine sulfate | 12.3000 |
| 2-aminoethanethiol HCl | 5.0000 |
| Thioglycolic acid | 2.4800 |
| Calcium hydroxide | 10.7900 |
| Cabosil HS-5* | 0.5000 |
| Stearyl alcohol | 7.5000 |
| Isocetyl alcohol | 5.5000 |
| Brij 56** | 4.3000 |
| Fragrance | 2.0000 |
| Coloring | 0.0125 |
| Water | 49.6175 |

*Fumed silica.
**Polyoxyethylene (10) cetyl ether (ICI Americas, Inc.)

EXAMPLE II

| Depilatory Gel | |
|---|---|
| Ceteareth 50* | 24.50 |
| Thiolglycerol | 6.00 |
| Aminoguanidine | 12.30 |
| Calcium hydroxide | 10.80 |
| Fragrance | 2.00 |
| Water | 44.40 |

*Polyethylene glycol ether of cetearyl alcohol.

Another embodiment of the present invention is as an aerosol. In such a form, the depilatory would include previously-listed optional ingredients as well as propellants. The following example presents such an aerosol. Again, it is meant merely as an illustration of the present invention and not limitative of that invention.

EXAMPLE III

| Depilatory Aerosol | |
|---|---|
| A. Concentrate | |
| Calcium thioglycolate | 7.48 |
| Aminoguanidine | 12.52 |
| Calcium hydroxide | 10.80 |
| Polyoxyethylene(20)stearylether | 4.30 |
| Stearyl alcohol | 7.50 |
| Mineral oil | 3.00 |
| Vaseline | 0.30 |
| Fragrance | 0.30 |
| Water | 53.80 |
| B. Fill | Grams |
| Concentrate | 176.00 |
| Propellant 12 | 7.12 |
| Propellant 114 | 5.38 |

What is claimed is:

1. An aqueous depilatory composition comprising:
   (a) from about 0.1M to about 2.0M of an active thiol agent; and
   (b) from about 0.01M to about 2.0M of aminoguanidine or its salts;
wherein said composition has a pH of from about 10.5 to about 12.5 at 25° C.

2. A depilatory composition as described in claim 1 wherein said active thiol agent is present at a level of from about 0.2M to about 1.0M.

3. A depilatory composition as described in claim 2 wherein said aminoguanidine is present at a level of from about 0.5M to about 1.0M.

4. A depilatory composition as described in claim 3 wherein said composition has a pH of from about 11.0 to about 12.3.

5. A depilatory composition as described in claim 4 wherein the active thiol agent is selected from the group consisting of thioglycolic acid, thiolactic acid, and B-mercaptopropionic acid, the alkali and alkaline-earth metal salts of these thiol acids, α-mercaptoethanol, thioglycerols, 1,3-dithio-2-propanol, 1,4-dithio-2-butanol, 1,4-dimercapto-2,3-butanediol, 1,3-dithio-2-methoxypropane, 1,3-dimercapto-2-aminopropane, 1,4-dimercapto-2,3-diaminobutane, and mixtures thereof.

6. A depilatory composition as described in claim wherein the active thiol agent is selected from the group consisting of thioglycolic acid, the alkaline-earth metal salts of said acid, and mixtures thereof.

7. A depilatory composition as described in claim 3, wherein said composition is a cream, lotion, or gel, and in addition contains from about 0% to about 5% of a filler, from about 0% to about 20% of an emulsifier, from about 0% to about 30% of a gelling agent or thickener, from about 0% to about 60% of an emollient, from about 0% to about 5% of a chelating agent, and from about 0% to about 5% fragrance and colorant.

8. A depilatory composition as described in claim 7, wherein said filler is selected from the group consisting of chalk, magnesium oxide and carbonate, clays, talc, fumed silica, and mixtures thereof.

9. A depilatory composition as described in claim 8, wherein said emulsifier is selected from the group consisting of anionic surfactants, nonionic surfactants, and mixtures thereof.

10. A depilatory composition as described in claim 9, wherein said thickener is selected from the group consisting of tragacanth, xanthan, karaya, and guar gums, clays, methyl or hydroxyethyl cellulose, hydroxypropyl cellulose, carboxymethyl cellulose, fatty and polyvinyl alcohols, modified sugars and starches, and mixtures thereof.

11. A depilatory composition as described in claim 10, wherein said emollient is selected from the group consisting of paraffin, petrolatum, mineral oil, fatty alcohols, silicone oils, and mixtures thereof.

12. A depilatory composition as described in claim 11, wherein said chelating agent is selected from the group consisting of ethylenediaminetetraacetic acids, the salts of said acids, and mixtures thereof.

13. A depilatory composition as described in claim 7 wherein said composition is an aerosol, and in addition contains from about 0% to about 20% propellant.

* * * * *

UNITED STATES PATENT OFFICE
CERTIFICATE OF CORRECTION

PATENT NO. : 4,618,344

DATED : October 21, 1986

INVENTOR(S) : Robert L. Wells

It is certified that error appears in the above-identified patent and that said Letters Patent are hereby corrected as shown below:

Column 4, Claim 6, line 1, after "claim" insert -- 5 --.

Signed and Sealed this

Third Day of February, 1987

Attest:

DONALD J. QUIGG

*Attesting Officer*  *Commissioner of Patents and Trademarks*